(12) United States Patent
Strombeck

(10) Patent No.: US 8,551,398 B1
(45) Date of Patent: Oct. 8, 2013

(54) DISINFECTANT HANDLE COVERING AND METHOD OF APPLYING

(76) Inventor: Steven Mark Strombeck, Eureka, CA (US)

(*) Notice: Subject to any disclaimer, the term of this patent is extended or adjusted under 35 U.S.C. 154(b) by 480 days.

(21) Appl. No.: 12/799,666

(22) Filed: Apr. 28, 2010

(51) Int. Cl.
*A61L 2/18* (2006.01)
*A61L 2/00* (2006.01)

(52) U.S. Cl.
USPC ............................................. 422/28; 422/291

(58) Field of Classification Search
USPC .................................................. 422/291, 28
See application file for complete search history.

(56) References Cited

U.S. PATENT DOCUMENTS 6,645,435 B2 * 11/2003 Dawson et al. ............... 422/110

2009/0249533 A1 * 10/2009 Sawalski et al. ................... 4/223

* cited by examiner

*Primary Examiner* — Kevin Joyner
(74) *Attorney, Agent, or Firm* — Risto A. Rinne, Jr.

(57) ABSTRACT

An apparatus for reducing the spread of infection includes a covering that is placed over a handle. A quantity of disinfectant that is disposed in an interior portion of the apparatus is expelled from the interior portion to an exterior surface of the apparatus when a user grasps and squeezes the covering or by gravity or by the use of a pump. The pump is activated at regular intervals or when the approach of a user is detected. The disinfectant is replenished or the apparatus is periodically replaced if an interior reservoir is used. If an outer reservoir is used the disinfectant is replenished or the reservoir is periodically replaced. A method for applying a disinfectant to an exterior surface of a covering is provided. According to a modification, the disinfectant is conveyed from the outer reservoir to an exterior surface of the handle by activation of the pump or by gravity if the reservoir is elevated above the handle. A method for applying a disinfectant to an exterior surface of a handle is provided.

15 Claims, 3 Drawing Sheets

DISINFECTANT HANDLE COVERING AND METHOD OF APPLYING

This application is related to an application entitled "Disinfectant Handle Covering" by the same inventor that is being filed concurrently with this application.

BACKGROUND OF THE INVENTION

1. Field of the Invention

The present invention, in general, relates to handles and, more particularly, to a disinfectant covering for a handle and method for applying a disinfectant to a surface of a handle.

Handles are widely used for a variety of reasons. Door handles are used to open doors. Faucet handles are used to control the flow of water through the faucet. A toilet handle is used to actuate a flushing cycle of the toilet. Numerous other varieties of handles are used to carry, move, actuate, or engage operation of some type of an object.

Many of these handles are in public places and are subject to frequent physical contact by members of the general population. There is risk that the spread of communicable diseases can be exacerbated by mutual contact with handles in public places.

If, for example, a carrier of an infectious disease that is transmittable through mutual touch (i.e., contact) with an object pushes on or otherwise makes contact with a public door handle that a person who is not a carrier of the infectious disease may later make contact with the same door handle within a period of time during which transmission of the disease remains viable through contact. If the person, after making contact with the door handle, acquires any of the infectious organisms there arises a risk of infection occurring to the person.

Depending on the nature and virulence of the microorganism the mechanisms for its transmission can vary greatly. For many microorganisms transmission of infection can occur in various ways, with some ways being more effective than others. For many organisms the likelihood of infection increases if, after having first made physical contact with a microorganism, the person then makes contact with one of their eyes or ears or with their nose or mouth. If contact with eyes, ears, nose, or mouth occurs within a period of time the microorganism may utilize the mucous membranes as a point of entry.

For many common types of microorganisms, such as varieties of the common cold, a resultant infection is usually mild. However, the potential for the occurrence of more serious consequences generally increases for the elderly and very young, as well as for those who may have a compromised immune response system or other contributing medical condition. Accordingly, less severe types of infectious disease, like the common cold, can expose people from these groups to a somewhat elevated level of risk of developing complication(s). However, for more serious infectious diseases, like influenza, the risk to people from these groups of developing especially severe or even life-threatening complications can increase significantly.

Therefore, people from these groups generally experience a greater desire than that of the general population to avoid contracting infection from communicable diseases, such as the common cold or influenza.

Additionally, the emergence of new pathogens, like H1N1 also occur and, depending on their severity, the immunity or lack thereof of the general populace, and their communicability, they may have the potential of causing widespread infection. Some can even cause epidemics or, worst case, world-wide pandemics. The infections produced by new pathogens may produce symptoms that are usually mild and only occasionally fatal, or they could be life-threatening for many of those who are unfortunate-enough to become infected. The uncertainty of the severity of infection that is associated with many newly discovered infectious strains can cause considerable fear of infection for much of the general populace.

An understanding of the transmission paths or mechanisms for transmission that can lead to the spread of infection from newly discovered pathogens may not be fully known for a period of time. This lack of knowledge can cause increased levels of fear among the general population who would prefer to play it safe by avoiding activities that they, as individuals, suspect may increase their chance of exposure to and possibly contracting a newly discovered microorganism. Therefore, people will generally wish to avoid the risk of transmission through mutual contact with an object, such as a handle in a public place, and especially so when relatively new and unknown pathogens are occurring in the populace.

It is useful to note that it is usually relatively easy, quick, and economical to identify various substances that if the substance is allowed to contact a [new] microorganism can kill or sufficiently weaken the microorganism sufficiently so that it does not pose a significant risk of spreading infection. However, learning about the vectors and mechanisms that spread infection or developing antibiotics to target the microorganism after it has entered into a person's body, by comparison, are likely to be far more difficult, slow, and costly to discover than identifying a number of substances that are capable of killing or weakening the microorganism by direct contact [exposure] with the microorganism. Testing to confirm the efficacy of substances capable of killing the microorganism upon making direct contact with the microorganism and that are safe for making contact with the human skin can often be completed well before deeper understandings or therapies for a newly discovered microorganism are attained.

This is especially significant because the potential benefits parallel the teachings of an old adage which states that, "An ounce of prevention is worth a pound of cure." Therefore, it is advantageous upon the discovery of a new pathogen to culture it and ascertain a substance that is effective in killing or weakening it upon contact. It is desirable to then use the substance(s) with the teachings herein to provide a means for preventing transmission through mutual touch. This has the potential to limit the size of outbreaks and save lives. Even if it is later determined that the new pathogen cannot be spread by mutual contact with an object, the psychological benefits of decreasing fear and anxiety and of not needlessly disrupting normal social patterns (like shopping at public stores) warrant the low cost of ensuring that this particular transmission vector (i.e., mutual contact with an object) is effectively blocked.

Also, changes or mutations in microorganisms can introduce new paths for infection. For example, infection by mutual contact with an object is a possible change for a microorganism that, previously, was not transmittable through mutual touch before.

Since most people will be required to push on a door handle in a public place to enter or exit the building or shopping mall there is ample opportunity for the transmission of germs or other agents that can cause infection to occur. The same is true when flushing a public toilet or when turning a faucet handle in a public bathroom. Microorganisms can be deposited on these and other objects in a variety of ways including, among others, mutual contact with an object (such as a handle of some type) by an infected person followed by contact with the object by a non-infected person and resulting in infection of the non-infected person, or by the infected person sneezing or coughing on the object followed by a second person making contact with the object and acquiring the microorganism, followed in turn by a third person making contact with the second person, such as by a handshake and resulting in infection of the third person.

Accordingly, there is a need to prevent the spread of disease for pathogens that are subject to transmission by mutual contact with a handle by infected and non-infected people in public places.

Similarly, in any private residence there are handles that many of the people who either live at the residence or visit there are likely to touch, such as a door handle, faucet handle, or toilet handle. Therefore, the risk of spreading infection by mutual contact with a handle also exists in a private residences.

Another area of acute need to control the spread of infection is in hospitals. A large percentage of those who visit a hospital when compared to the population at large are ill. Some come as patients who are treated and leave that day while others are admitted for a period of time. Visitors, family, or friends of patients may also be carriers of various infectious diseases as can the patients themselves. In general, hospitals can become a locus for the accumulation and transmission of infectious agents.

Accordingly, the numerous door handles, lavatory faucet handles, water cooler handles, and other handle surfaces that people are likely to make contact with in the hospital are especially prone to accumulating contagious microorganisms, thereon. Aside from an increased risk of contagion, in general, occurring in hospitals, certain of the patients may be at elevated levels of risk of being infected (even from a brief or otherwise limited exposure to microorganisms that would not normally result in the transference of infection to most healthy people) or of developing serious consequences from an infection (even as a result of exposure to a relatively benign type of microorganism) due to their weakened physical state or compromised immune response.

Therefore, taking reasonable precautions that help prevent the spread of infection is generally wise for all communicable diseases and especially so for more virulent or dangerous pathogens, or for newer microorganisms. This is true for all public areas, hospitals, commercial establishments and, in general, wherever the potential exists for the spread of disease including private residences.

There is a practice that illustrates the need for a solution to the long-standing problem of reducing the spread of infection arising through mutual contact with handles in public places. Many people, for example, after using the facilities in a public restroom and after having washed their hands will use the paper towel that was used to dry their hands as an intermediate or barrier layer as they grasp (i.e., make contact with) a handle used to open the door leading to or from the public restroom, unlatch the door, and open the door to exit the restroom. This practice is accomplished by an increasing number of people because they wish to avoid having any portion of their hands make contact with the door handle and risk the possible transference of a harmful microorganism (i.e., a germ, bacteria, virus or other pathogen) from the door handle to their hands and of possibly acquiring an infection (i.e., a cold, flu, bacterial infection, etc.) as a result.

When a trash can is located by the restroom door most people who engage in this particular practice will attempt to deposit their used paper towel in the trash can (wastebasket) after opening the door to exit. If no trash can is available they may discard their paper towel on the floor proximate the door rather than carry the used paper towel after exiting and then search for a trash can outside of the restroom to deposit the paper towel in. This can result in unsightly debris accumulating proximate the door of the public restroom.

Not only are the discarded paper towels unsightly, but they are also dangerous as they pose a slipping hazard. If the discarded paper towels contain a quantity of residual soap after a person has washed his or her hands, they can be quite slippery thereby creating an especially hazardous condition in the restroom that could result in a fall and possible serious injury. This can increase suffering for the individual who slips and it can increase liability for the owner(s) of the facility. It is for this reason that additional trash cans are more frequently being placed near the entrance door at an increasing number of public restrooms. Increasing the number of wastebaskets in public restrooms increases janitorial costs as there are now multiple wastebaskets to empty and clean. Discarding paper towels on the floor, of course, also increases janitorial expenses.

Also, some people will dispense a second, clean paper towel for use solely in opening the restroom door. This practice increases waste and the consumption of natural resources, and it contributes negatively to the premature filling of landfills and hastens the unwanted release of greenhouse gases ($CO_2$) into the atmosphere.

The growing practice of using paper towels to open the restroom door when leaving the restroom further illustrates the need for providing an effective solution to this problem. As new diseases are being discovered and as people continue to become ever more health-conscious the need to help prevent the spread of infection (i.e., contagion) in public places is steadily increasing.

Therefore, there is a long-standing need for a solution that lessens the likelihood of the transference of infectious (i.e., communicable) diseases in public places. Similarly, there is long standing need to reduce litter in restrooms. There is also a need to lessen the use of paper towels, thereby conserving natural resources, decreasing landfill demand, and lessening the release of greenhouse gases into the atmosphere.

In addition, there is a growing need to both increase safety, decrease injuries and liability, and to also instill a feeling of increased safety among the general public as far as the possibility of a non-infected person contracting a communicable disease from an infected person through the vector of contagion via mutual contact occurring whereby the non-infected person makes contact with a handle following contact with the handle by the infected person.

Absent the availability of an effective solution there is evidence of increasing fear and of increasing avoidance behaviors occurring among the general population. Some avoidance behaviors may border on what appears to be irrational or excessive types of avoidance behavior. Fear supplies the motive force behind all such avoidance behaviors.

For example, certain people now carry a commercially available type of liquid disinfectant with them wherever they go and they apply it to their hands after contact with any person or object has occurred. Some people have adopted a multi-level hand cleaning and disinfecting process that includes cleansing with antimicrobial hand soap, followed by the use of a commercially available liquid disinfectant, followed again by a rinsing and drying of their hands using a second type of disinfectant, such as isopropyl alcohol. These types of behaviors are becoming far more commonplace today than they were even a decade ago. Certain of the commercially available antimicrobial hand cleaning or liquid (or gel) disinfectant products that are in widespread use today were not even available ten to twenty years ago.

The general level of anxiety or fear increases whenever a new virus or infectious microorganism is discovered. If an especially virulent new disease captures the interest of the news media, or when there is talk of a possible epidemic or pandemic, the general level of fear rises sharply. If the fear becomes sufficiently strong, people will avoid going to public places unless absolutely necessary. This can, for example, cause a significant drop in consumer spending (i.e., shopping) resulting from a decreased willingness to shop and risk exposure in public places. This, in turn, can contribute toward a potentially severe economic downturn.

Accordingly, there is a need for a product that promotes a feeling of safety as far as its efficacy in reducing or even preventing the spread of (certain) communicable diseases is concerned. Such a product would also cause a desired decrease to occur in the level of anxiety or fear that is experienced.

Additionally, certain of the prior art solutions have not provided a satisfactory solution to these problems or gained widespread usage for a variety of reasons. For example, some prior art solutions rely on a disinfectant vapor to kill microorganisms. However, a user cannot see, feel, or otherwise perceive the existence of the vapor. Accordingly, the user is apt to believe that the device is not working or that it is old and void of the disinfectant material even when it is functioning properly. Therefore, the user might not feel safe using such a device.

Gaining consumer acceptance for such a type of device may require educating a user to increase the user's understanding of how the device operates before the user would be inclined to rely on it. Educating the public can take time or be costly to accomplish. Even after being educated sufficiently to realize that vapors are being used to disinfect an object rather than experiencing direct contact with a perceptible liquid or gel disinfectant, the user may still prefer the security that comes when they know that their hands have made perceptible contact with a quantity of the disinfectant material.

Also, certain other types of prior art devices provide a release of a disinfectant that diminishes over time and/or use. Therefore, the efficacy of the device decreases over the course of time and use. The device may provide adequate efficacy when it is new, however, the efficacy may significantly decline over the course of time or use as the disinfectant is progressively consumed, with a greater dose of disinfectant than is needed being administered when the device is new and a lesser dose of disinfectant than is needed being administered after the passage of time and after the device has been used a sufficient amount. Also, there may not be an adequate indication as to when the device (or the disinfectant in the device) needs replacement or replenishing.

There is also another need and that is to reduce the time required by an individual to prevent or lessen the likelihood of contagion occurring. It takes time for a person to dispense and apply a disinfectant to his or her hands and wipe their hands to spread the disinfectant over the skin surface. This can cause crowding in restrooms and delay access to faucets or paper towel dispensers.

There is a need to reduce the time required to sterilize the hands of those who may come in contact with infectious microorganisms.

A device that continually provided a sterile surface would be especially ideal. In that situation a (non-infected) person who, after having made contact with the surface, would not have any real need to apply a disinfectant to their hands if the person knew that the surface, itself, had already been disinfected (i.e., if the surface was sterile or sufficiently sterilized). In other words, if the surface was able to kill or sufficiently weaken the greater percentage of microorganisms that had been deposited on it by an infected person, those people who later have contact with the surface would be considerably less likely to acquire the infection. For all practical purposes, the likelihood of contagion could be reduced to zero. In this situation there would be no additional time burden placed on the non-infected person. If the surface was, for example, a handle of a door in a public restroom, the person could simply contact the door handle, open the door, and leave without any further action or consideration being required, knowing that the door handle could not possibly contain and transmit any viable (i.e., infectious) pathogens to the person.

Therefore, there is a need for a device and method to squeeze, force or expel out of an interior portion of a handle covering and onto an exterior surface of the handle covering a quantity of disinfectant, wherein a portion of the disinfectant is transferred to a hand or hands of a user when the user makes contact with the exterior surface of the handle covering.

There is also a need for a device and method to provide, in combination, a desired type and a desired quantity of a disinfectant on an exterior surface of a handle covering, wherein a portion of the disinfectant is transferred to a hand or hands of a user when the user makes contact with the exterior surface of the handle covering, and wherein the user is able to perceive (i.e., feel) the presence of at least some of the portion of the disinfectant that was transferred to their hand or hands after having made contact with the exterior surface of the handle covering.

There is also a need for a device and method that expels a desired quantity of a disinfectant out of an interior portion of a handle covering and onto an exterior surface of a handle covering periodically to ensure that the desired quantity of the disinfectant is present on the exterior surface of the handle covering prior to or at the time that the user makes contact with the exterior surface of the handle covering.

There is also a need for a device and method that applies a desired quantity of a disinfectant to a surface of a handle, wherein a portion of the disinfectant is transferred to a hand or hands of a user when the user makes contact with the surface of the handle.

There is also a need for a device and method that applies a desired type of a disinfectant and a desired quantity of the desired type of the disinfectant to the surface of a handle, wherein a portion of the disinfectant is transferred to a hand or hands of a user when the user makes contact with the surface of the handle, and wherein the user is able to perceive (i.e., feel) the presence of at least some of the portion of the disinfectant that was transferred to their hand or hands after having made contact with the surface of the handle.

There is also a need for a device and method that applies a desired quantity of a disinfectant to a surface of a handle periodically to ensure that the desired quantity of the disinfectant is present on the surface of the handle prior to or at the time that the user makes contact with the surface of the handle.

Accordingly, there exists today a need for a disinfectant handle covering and method of applying a disinfectant to a handle that helps to ameliorate the above-mentioned problems and difficulties as well as ameliorate those additional problems and difficulties as may be recited in the "OBJECTS AND SUMMARY OF THE INVENTION" or discussed elsewhere in the specification or which may otherwise exist or occur and that are not specifically mentioned herein.

As different embodiments of the instant invention help provide a more elegant solution to the various problems and difficulties as mentioned herein, or which may otherwise exist or occur and are not specifically mentioned herein, and by a showing that a similar benefit is not available by mere reliance upon the teachings of relevant prior art, the instant invention attests to its novelty.

Therefore, by helping to provide a more elegant or effective solution to various needs, some of which may be long-standing in nature, the instant invention further attests that the elements thereof, when related in the specific combination(s) as claimed herein, are novel and that the claimed structures cannot be deemed as obvious variants of the prior art device (s) by a person possessing ordinary ability or ordinary creativity in the relevant field(s) of art when the presently claimed structures are viewed in light of the specific teachings of the prior art, and when the viewing of the prior art is accompanied by a consideration of the purpose(s) of the prior art, the problem(s) solved by the prior art, and the efficacy of the improvements provided by the prior art when compared to the instant invention.

Clearly, such an apparatus would be useful and desirable.

2. Description of Prior Art

Door handle covers and sanitary devices are, in general, known. For example, the following patents describe various types of these devices, some of which may have relevance as well as others which may not have particular relevance to the invention. These patents are cited not as an admission of their having any particular relevance to the invention but rather to present a broad and diversified understanding regarding the current state of the art appertaining to either the field of the invention or possibly to other related or distal fields of invention.

U.S. Pat. No. 6,546,594 to Wills, that issued on Apr. 15, 2003;
U.S. Pat. No. 6,499,155 to Barrios, that issued on Dec. 31, 2002;
U.S. Pat. No. 4,856,140 to Visco et al., that issued on Aug. 15, 1989;
U.S. Pat. No. 4,832,942 to Crace, that issued on May 23, 1989; and
U.S. Pat. No. 1,491,780 to Abbott, that issued on Apr. 29, 1924;
and including Statutory Invention Registration:
U.S. Statutory Invention Registration No. H2137 to Newman et al., that published on Jan. 3, 2006;
and including Patent Applications Publications:
U.S. Patent Application Publication No. 2009/0065112 to Polakow, that published on Mar. 12, 2009;
U.S. Patent Application Publication No. 2009/0000060 to Edens, that published on Jan. 1, 2009;
U.S. Patent Application Publication No. 2006/0230576 to Meine, that published on Oct. 19, 2006;
U.S Patent Application Publication No. 2006/0059663 to D'Ambrosio, that published on Mar. 23, 2006; and
U.S. Patent Application Publication No. 2006/0010652 to Kellaher et al., that published on Jan. 19, 2006.

While the structural arrangements of the above described devices may, at first appearance, have similarities with the present invention, they differ in material respects. These differences, which will be described in more detail hereinafter, are essential for the effective use of the invention and which admit of the advantages that are not available with the prior devices.

OBJECTS AND SUMMARY OF THE INVENTION

It is an object of the present invention to provide a disinfectant handle covering and method of applying a disinfectant to a handle that ensures the release of a disinfectant when contact is made with the handle.

It is also an important object of the invention to provide a disinfectant handle covering and method of applying a disinfectant to a handle that includes a quantity of a disinfectant inside of a handle covering that is expelled to an exterior of the handle covering when a user grasps and squeezes the handle covering.

Another object of the invention is to provide a disinfectant handle covering and method of applying a disinfectant to a handle that includes a quantity of a disinfectant inside of a handle covering that is expelled to an exterior of the handle covering at a regular predetermined spaced-apart time interval.

Still another object of the invention is to provide a disinfectant handle covering and method of applying a disinfectant to a handle that includes a quantity of a disinfectant inside of a handle covering that is expelled to an exterior of the handle covering whenever the occurrence of a trigger event is detected, such as detection of the approach of a person toward the handle covering.

Still yet another object of the invention is to provide a disinfectant handle covering and method of applying a disinfectant to a handle that includes a quantity of a disinfectant inside of a handle covering that is expelled to an exterior of the handle covering by gravity.

Yet another important object of the invention is to provide a disinfectant handle covering and method of applying a disinfectant to a handle that includes a quantity of a disinfectant inside of a handle covering that is expelled to an exterior of the handle covering by activation of a pump or motor.

Still yet another important object of the invention is to provide a disinfectant handle covering and method of applying a disinfectant to a handle that provides a tangible indication to a user that contact has been made with the disinfectant.

A first continuing object of the invention is to provide a disinfectant handle covering and method of applying a disinfectant to a handle that is adaptable for use with a variety of different types or different shapes of handles.

A second continuing object of the invention is to provide a disinfectant handle covering and method of applying a disinfectant to a handle that is disposable.

A third continuing object of the invention is to provide a disinfectant handle covering and method of applying a disinfectant to a handle that is able to kill or sufficiently weaken at least some of a quantity of certain microorganisms that are deposited on a surface of the disinfectant handle covering.

A fourth continuing object of the invention is to provide a disinfectant handle covering and method of applying a disinfectant to a handle that provides a way to automatically kill or weaken microorganisms that are left on the handle after contact by an infected person.

A fifth continuing object of the invention is to provide a disinfectant handle covering and method of applying a disinfectant to a handle that provides a way to automatically kill or weaken microorganisms that are left by an infected person on a handle and transferred to the hand or hands of a non-infected person who then comes in contact with the handle.

A sixth continuing object of the invention is to provide a disinfectant handle covering and method of applying a disinfectant to a handle that expels a quantity of disinfectant out of an interior portion of a handle covering to an exterior surface of the handle covering, whereby a portion of the disinfectant is transferred to a hand or hands of a user when the user makes contact with the exterior surface of the disinfectant handle covering.

A seventh continuing object of the invention is to provide a disinfectant handle covering and method of applying a disinfectant to a handle that provides a desired quantity of a desired type of a disinfectant on an exterior surface of a handle covering, wherein a portion of the disinfectant that is on the exterior surface of the handle covering is transferred to a hand or hands of a user when the user makes contact with the exterior surface of the handle covering, and wherein the user is able to perceive the presence of at least some of the portion of the disinfectant that was transferred to their hand or hands after having made contact with the exterior surface of the handle covering.

An eighth continuing object of the invention is to provide a disinfectant handle covering and method of applying a disinfectant to a handle that that expels a quantity of disinfectant out of an interior portion of a handle covering to an exterior surface of the handle covering periodically, thereby ensuring that a desired quantity of the disinfectant is present on the exterior surface of the handle covering prior to or at the time the user makes contact with the exterior surface of the handle covering.

A ninth continuing object of the invention is to provide a disinfectant handle covering and method of applying a disinfectant to a handle that applies the disinfectant to a surface of the handle, wherein a portion of the disinfectant is transferred to a hand or hands of a user when the user makes contact with the surface of the handle.

A tenth continuing object of the invention is to provide a disinfectant handle covering and method of applying a disinfectant to a handle that applies a desired quantity of a disinfectant to a surface of a handle wherein, a desired type and a desired quantity of the desired type of the disinfectant are applied to the surface of the handle, wherein a portion of the disinfectant is transferred to a hand or hands of a user when the user makes contact with the surface of the handle, and wherein the user is able to perceive (i.e., feel) the presence of at least some of the portion of the disinfectant that was transferred to their hand or hands after having made contact with the surface of the handle.

An eleventh continuing object of the invention is to provide a disinfectant handle covering and method of applying a disinfectant to a handle that includes a quantity of a disinfectant inside of a handle covering that is expelled to an exterior of the handle covering during use, and wherein a portion of the quantity of the disinfectant inside of the handle covering is eventually depleted, and wherein the portion of the quantity of the disinfectant inside of the handle covering is replenishable.

A twelfth continuing object of the invention is to provide a disinfectant handle covering and method of applying a disinfectant to a handle that includes a reservoir of disinfectant disposed above a handle and including means for conveying a quantity of the disinfectant in the reservoir to an exterior surface of the handle.

A thirteenth continuing object of the invention is to provide a disinfectant handle covering and method of applying a disinfectant to a handle that includes a reservoir of disinfectant disposed proximate a handle and including means for conveying a quantity of the disinfectant in the reservoir to an exterior surface of the handle.

A fourteenth continuing object of the invention is to provide a disinfectant handle covering and method of applying a disinfectant to a handle that includes a reservoir of disinfectant disposed proximate a handle and including means for conveying a quantity of the disinfectant in the reservoir to an exterior surface of the handle at a regular predetermined periodic interval.

A fifteenth continuing object of the invention is to provide a disinfectant handle covering and method of applying a disinfectant to a handle that includes a reservoir of disinfectant disposed proximate a handle and including means for conveying a quantity of the disinfectant in the reservoir to an exterior surface of the handle whenever the occurrence of a trigger event is detected, such as detection of the approach of a person toward the handle covering.

Briefly, according to a first embodiment a disinfectant handle covering that is constructed in accordance with the principles of the present invention includes a quantity of a disinfectant in an interior portion of the disinfectant handle covering, a portion of which is forced out of the interior portion and expelled to an exterior of the disinfectant handle covering when a user grasps and squeezes the disinfectant handle covering. Alternately, the portion of the disinfectant that is expelled is forced out by gravity. Alternately, the portion of the disinfectant that is expelled is forced out by the periodic activation of a pump or motor at a regular predetermined interval.

Alternately, the portion of the disinfectant that is expelled is forced out by the periodic activation of a pump or motor subsequent to the occurrence of a trigger event, such as detection of the approach of a person toward the disinfectant handle covering which results in a timed activation of the pump or motor. Preferably, the portion of the disinfectant that is expelled during use is replenishable. Alternately, the disinfectant handle covering is replaced when the disinfectant in the interior portion has been used or it is replaced at regular intervals to ensure that replacement occurs prior to the complete depletion of the disinfectant in the interior portion. According to a second embodiment, a reservoir containing a quantity of disinfectant is placed proximate a handle and a quantity of the disinfectant is conveyed from the reservoir to an exterior surface of the handle by gravity, or automatically at regular intervals by the periodic activation of a pump or motor, or by the periodic activation of a pump or motor subsequent to the occurrence of a trigger event, such as detection of the approach of a person toward the handle. If gravity supplies the force for conveyance of the disinfectant to the exterior surface of the handle the reservoir is disposed at a higher elevation than the elevation of the handle. Preferably, the quantity of the disinfectant in the reservoir is replenishable. Otherwise, the reservoir is periodically replaced with a new, full reservoir when empty or at regular predetermined intervals.

DETAILED DESCRIPTION OF THE INVENTION

Figure 1:
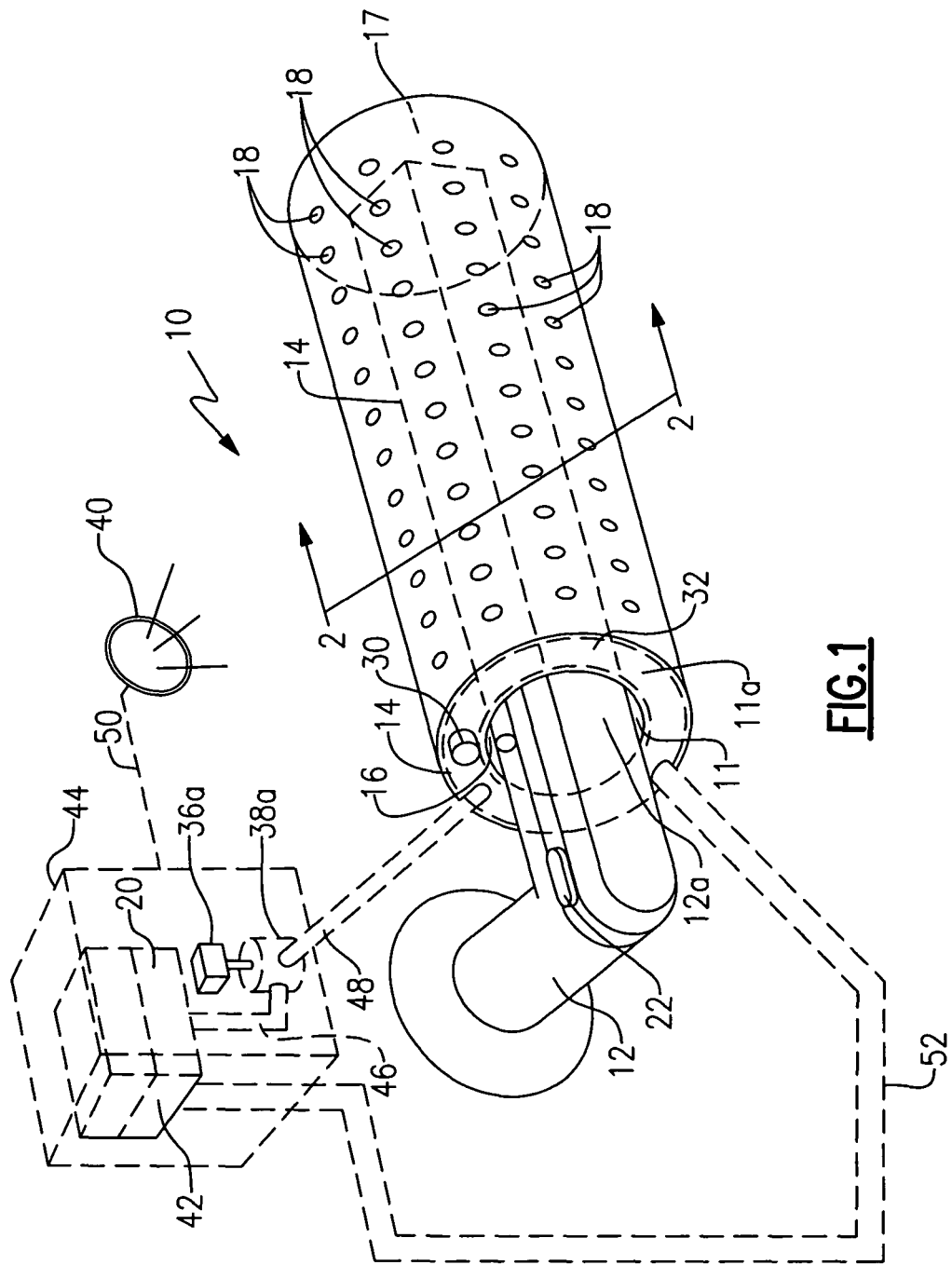
FIG. 1 is a view in perspective of a disinfectant handle covering that is disposed over a handle.
Figure 2:
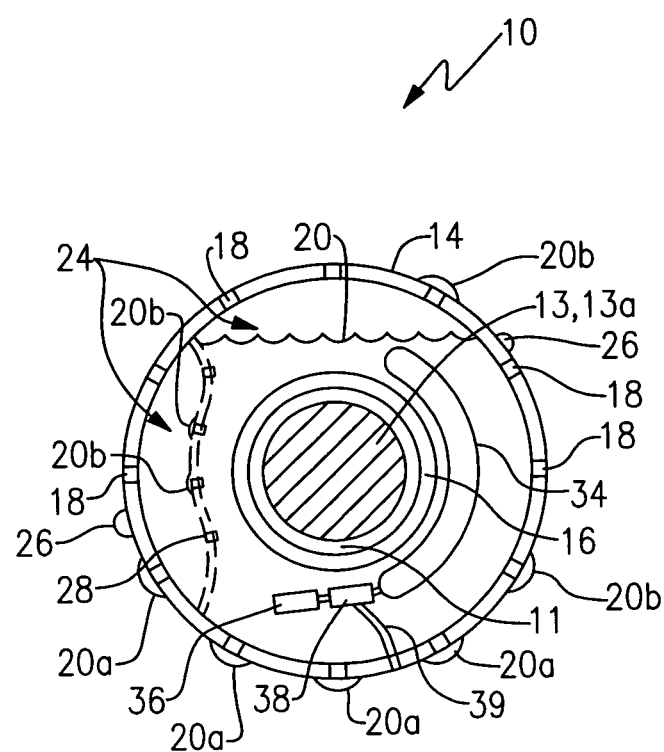
FIG. 2 is cross-sectional view taken along the line 2-2 of the disinfectant handle covering of FIG. 1 with a round handle substituted for the square handle of FIG. 1.

Referring on occasion to all of the FIGURE drawings and now, in particular to FIG. 1 and to FIG. 2, is shown a disinfectant handle covering, identified in general by the reference numeral 10.

The reader will notice that reference is occasionally made throughout the DETAILED DESCRIPTION OF THE INVENTION suggesting that the reader refer to a particular drawing FIGURE. The suggestion is at times made when the introduction of a new element requires the reader-to refer to a different drawing FIGURE than the one currently being viewed and also when the timely viewing of another drawing FIGURE is believed to significantly improve ease of reading or enhance understanding. To promote rapid understanding of the instant invention the reader is encouraged to periodically refer to and review each of the drawing FIGURES for possible cross-referencing of component parts and for other potentially useful information.

The disinfectant handle covering 10 is disposed over a handle 12. The handle 12 includes any type of handle that is used for any desired purpose. The handle 12, for example, can be the type that is used to open a door or to flush a toilet. Depending on the size, shape, and motion that is required to actuate the handle 12, the disinfectant handle covering 10 is modified to fit the handle 12 and to maintain its position on the handle 12 throughout the range of motion exhibited by the handle 12.

For example, the disinfectant handle covering 10 can include a cylindrical-shaped center opening 11, as shown, that includes a circular cross-section or, if desired, a square, rectangular, oval or other shape can be used for the center opening 11 to fit any desired shape of the handle 12. The center opening 11 includes an open end 11a and extends into an interior of the disinfectant handle covering 10 a sufficient amount to permit an elongated section 12a of the handle 12 to be inserted in the center opening 11 any desired amount.

The disinfectant handle covering 10 includes an outer layer 14 that must be made from a flexible material. The outer layer 14 is discussed in greater detail hereinafter. The disinfectant handle covering 10 includes an inner layer 16 that may be made (formed) from a rigid or flexible material.

A distal end member 17 is attached to the outer layer 14 and to the inner layer 16. The distal end member 17 provides an end covering for the disinfectant handle covering 10 and a seal over the center opening 11. The distal end member 17 also provides a seal that extends around the circumference or perimeter of the outer layer 14 and around the circumference or perimeter of the inner layer 16.

If the inner layer 16 is formed of a more rigid type of material, the cross-section of the center opening 11 is preferably the same as that of the handle 12, only slightly larger in order to accommodate insertion of the elongated section 12a of the handle 12 up to the longitudinal length of the center opening 11.

If, however, the inner layer 16 is formed of an especially flexible type of material, the cross-sectional shape of the center opening 11 is less critical as it can adjust to accommodate the cross-sectional shape of the handle 12. For example, if the handle 12 (as shown in FIG. 1) includes a square cross-sectional shape, even a circular shaped (in cross-section) center opening 11 will alter its shape to accommodate the differently-shaped elongated section 12a of the handle 12 (it will become more square in cross-section) providing that the inner layer 16 is formed from a sufficiently flexible material. Refer to FIG. 2 is shown a modified elongated section 13a of a modified handle 13 that includes a circular cross-section. This illustrates the ability of the disinfectant handle covering 10 to adjust and accommodate different sizes and types of the handles 12, 13.

To install the disinfectant handle covering 10 the open end 11a of the center opening 11 is aligned with and urged on the elongated section 12a, 13a, of the handle 12, 13 until a desired longitudinal length of the elongated section 12a, 13a of the handle 12, 13 is inserted in the center opening 11. Preferably, the disinfectant handle covering 10 will cover the portion of the elongated section 12a, 13a that a user is likely to make contact with as he or she grasps the disinfectant handle covering 10 to actuate the handle 12, 13.

If desired, the inner layer 16 can be formed from a material (i.e., an elastomer) that is both flexible and elastic. This would permit some degree of stretching (i.e., expansion) by the inner layer 16 thereby adapting any given version of the disinfectant handle covering 10 for possible use with an expanded range (i.e., a greater number) of possible styles and shapes of the handle 12. Accordingly, fewer different versions of the disinfectant handle covering 10 may be required if the inner layer 16 is formed from a flexible and elastomeric type of material.

The outer layer 14 is formed of a planar sheet of flexible material that, when the disinfectant handle covering 10 is installed on the handle 12, encircles the elongated section 12a of the handle 12. The outer layer 14 can include any desired cross-sectional shape to provide optimum appearance and/or similarity with respect to the cross-sectional shape of the elongated section 12a of the handle 12.

The inner layer 16 is formed of a continuous or contiguous sheet of material that is not porous to a liquid or gel at room temperature. The outer layer 14 includes a large number of small diameter perforations 18 (holes) that extend around an outside surface of the disinfectant handle covering 10.

The perforations 18 are sufficiently numerous and small-enough in size so that a disinfectant 20 fluid or gel that is contained within the disinfectant handle covering 10 will not continue flowing through the perforations 18 by the force of gravity and drain the disinfectant 20 fluid or gel from the disinfectant handle covering 10.

For certain versions of the disinfectant handle covering 10 it is permissible for a small predetermined quantity of the disinfectant 20 fluid or liquid to flow through some of the perforations 18 and accumulate proximate the perforations 18 at or near the bottom of the disinfectant handle covering 10 by force of gravity. See reference numeral 20a, FIG. 2.

If the size of the perforations 18 is small enough, then the surface tension of the disinfectant 20 fluid or gel will retain the disinfectant 20 that has accumulated on the outside surface of the outer layer 14 proximate to the lower perforations 18 and thereby prevent a continuous rate (or condition) of flow from occurring.

By controlling the viscosity of the disinfectant 20 fluid or gel in relation to the opening size of the perforations 18 it is possible to control the amount of the disinfectant 20 fluid or gel that will flow by the force of gravity and accumulate on the outside surface of the outer layer 14 around the lower perforations 18 (as shown by 20a). If the opening size of the perforations 18 is sufficiently small or the viscosity too great, then no disinfectant 20 fluid or liquid will flow out of (i.e., through) the perforations 18 if urged only by the force of gravity.

As shown, the disinfectant handle covering 10 covers a portion of the handle 12. Ideally, the disinfectant handle covering 10 will cover the likely portions of the handle 12 that a user is likely to come in contact with when his or her hand (not shown) touches the handle 12 during use. If desired, the disinfectant handle covering 10 can be made as large as desired to cover as much of the handle 12 as is desired.

If a friction-fit is desired, the center opening 11, which is formed by the inside surface of the inner layer 16 engages frictionally with the elongated section 12a of the handle 12. If desired, a hook and loop type of a strap 22 can be used to secure the disinfectant handle covering 10 to the handle 12, 13.

Other methods for securing the disinfectant handle covering 10 to any type of the handle 12, 13 are also possible. It is also understood that any embodiment of the disinfectant handle covering 10, as disclosed herein, can be modified to fit any desired type of the handle 12 that is known or will be known. If desired, an adhesive can be used to secure a modified version (not shown) of the disinfectant handle covering 10 to a type of a handle (not shown) that only provides limited access to the handle or which does not permit access to occur fully around a circumference of the handle.

For example, certain public doors include a rectangular elongated type of the handle that is disposed in a surrounding enclosure. The user depresses the rectangular elongated (elevated) portion to unlatch the door. The user continues to depress the elongated portion of the handle to urge the door to swing open. An adhesive can used to secure the disinfectant handle covering 10 to this type of a handle. Modification to include a "C-shaped" clamp as part of a modified version of the disinfectant handle covering 10 may also provide a way of securing the disinfectant handle covering 10 to the elongated portion or to other types of the handle.

Other public doors may include an elongated type of handle (not shown) that does not include an open end. The elongated portion of this type of handle can include a cross-sectional shape that is circular, oval, square, rectangular, or otherwise. Both opposite ends of the elongated portion of this type of the handle are secured by an enclosure and other hardware of the door latch.

If desired, an adhesive may also be used to secure a modified planar version of the disinfectant handle covering 10 that has been sized to wrap around the elongated portion of this type of the handle. Or, if desired, the disinfectant handle covering 10 can be modified to include separable symmetrical longitudinal halves that include members attached to the two halves and fasteners, like machine screws, that cooperate with each of members on both halves to secure the two halves together and thereby encircle the elongated portion of this type of the handle.

Referring again to FIG. 2, the disinfectant 20 is disposed between the inner layer 16 and the outer layer 14 in an inner reservoir, identified in general by the reference numeral 24, of the disinfectant handle covering 10.

The disinfectant 20 chosen is selected for its efficacy in killing or weakening a quantity of microorganisms 26 that are deposited by an infected person (not shown) and which accumulate on the outside surface of the outer layer 14. Preferably, the disinfectant 20 is effective at killing or sufficiently weakening a broad spectrum of different types of the microorganisms 26 so as to hinder or prevent the spread of infection.

It is also possible to selectively choose a type of the disinfectant 20 for use with any version of the disinfectant handle covering 10 that specifically targets a particular type (i.e., strain) of the microorganisms 26 or to choose a type of the disinfectant 20 that targets a desired group of the microorganisms 26, as desired. For example, if a new virulent pathogen has been discovered and the microorganisms 26 are representative of the new pathogen, then to help prevent the occurrence of an epidemic or pandemic the preferred disinfectant 20 that is selected would likely be chosen to kill or weaken this particular pathogen as its most important attribute or highest priority.

If the disinfectant 20 that was chosen because of its efficacy in killing or weakening the new pathogen also proved effective in killing or weakening a broader spectrum (i.e., a wider range) other types of the microorganisms 26 that included other undesirable types of the microorganisms 26 which cause or contribute to the spread of communicable diseases that would, of course, be even better.

It is also important to note that the disinfectant 20 can include a mixture, solution, or blending of various different types of the disinfectant 20 providing that the desired efficacy in killing or weakening the most important or targeted microorganisms 26 remains at a sufficiently high, desired level.

During use, in order to activate whatever is controlled by the handle 12, the user will attempt to grasp the elongated section 12a of the handle 12. The handle 12, or any differently shaped version thereof, may be used to flush a toilet, open a door, control the flow of water through a faucet, actuate a mechanism of some sort, etc. The handle 12 could even be one of a number of push-buttons in an elevator.

Basically, the handle 12 represents any surface that a user is either likely to, or which the user may be required to contact, such as a door handle in order to enter or exit an area, room, or building. The handle 12 does not actually have to move relative to an object that it is affixed to.

For example, the handle 12 could be a "push-plate" on a door that the user would push to open the door. Certain doors are not latched, but merely swing open for entry or exit. The push-plate includes a surface that is provided for the user to contact. The disinfectant handle covering 10 is modified to cover the area of the planar push-plate and is attached to the push-plate by any preferred method, including the use of an adhesive or any desired type of fastener(s). If desired, a hook and loop fastener could be used with the push-plate or with any version of the disinfectant handle covering 10 to permit rapid removal and reattachment or replacement of the disinfectant handle covering 10.

When the user attempts to grasp the elongated section 12a of the handle 12 the hand of the user grasps and naturally squeezes the outside surface of the outer layer 14. This action supplies a force to the outer layer 14 that compresses a portion of the outer layer 14 and, thereby, urges a portion of the outer layer 14 toward the inner layer 16. Also, if the handle 12 is pulled or pushed, an additional force is applied to the outer layer 14 that also urges a portion of the outer layer 14 toward the inner layer 16.

Compressing the outer layer 14 results in the temporary formation of a distorted outer layer 28 (as illustrated in FIG. 2 by dashed lines 28). It is assumed that the fingers of the user have urged the outer layer 14 inward thereby forming the distorted outer layer 28. Due to the preferred elastomeric property of the outer layer 14 it will rebound to its original shape as shown in FIG. 2 when the user's grasp is removed and the inward force exerted upon the outer layer 14 ceases.

Compressing the outer layer 14 applies an increased pressure on the disinfectant 20 that is disposed (contained) in the inner reservoir 24. This forces an additional predetermined quantity of the disinfectant 20b to flow out of (i.e., through) at least some of the perforations 18. The disinfectant 20 can be either in the form of a liquid or gel-like material.

Some of the additional predetermined quantity of the disinfectant 20b contacts the fingers and hands of the user. When the user releases contact with the disinfectant handle covering 10 some of the additional predetermined quantity of the disinfectant 20b will remain on the fingers and hands of the user. The user may perceive this quantity and would naturally be inclined to rub their hands together. This action would spread the disinfectant 20 on the surface of the user's hands, thereby effectively killing or weakening (i.e., sterilizing) any of the microorganisms 26 that may also have been transferred to the user's hands.

If preferred, the disinfectant 20 is modified to include a sufficiently volatile substance or base, for example isopropyl alcohol, that evaporates quickly. If this type of modified disinfectant 20 is used, the user would not even need to rub their hands together as the small quantity of the disinfectant 20 that transferred from the disinfectant handle covering 10 to their hands would soon quickly evaporate on its own. Of course, the user could still rub their hands together to hasten the evaporation process.

Some or even all of the microorganisms 26 that are deposited on the outside surface of the outer layer 14 may be killed or weakened by a residual amount of the disinfectant 20 that remains on the outside surface of the outer layer 14 after the disinfectant handle covering 10 has been grasped or otherwise contacted by the user and then released. This is important to note because the microorganisms 26 that the user acquires by contact with the disinfectant handle covering 10 may no longer be alive or viable (capable) of spreading infection.

In this situation the user would not need to do anything, like rub their hands to spread the disinfectant 20 around, because there would be virtually no risk of acquiring infection through the spread of an infectious pathogen as a result of the benefit provided by the disinfectant handle covering 10.

However, if the user were to rub their hands they would be spreading the acquired disinfectant 20 over the surface of their hands and in this way killing any viable microorganisms 26 that they may have acquired from having had earlier contact with or exposure to another source of infection.

Accordingly, a significant unexpected benefit is provided by the disinfectant hand covering 10 (all versions) in which it also helps to prevent infection of the user by pathogens the user has acquired from sources other than from the disinfectant hand covering 10.

Another possible modification is to provide a more rigid version of the outer layer 14 and to select a desired type and viscosity for the disinfectant 20 while also providing a desired number of the perforations 18 proximate a bottom of the disinfectant handle covering 10 only. The size of the perforations 18 would then be set to ensure that by the force of gravity some of the disinfectant 20 flows through and accumulates (see 20a, FIG. 2) proximate at least some of the perforations 18.

The more rigid version of the outer layer 14 does not significantly compress or expel an additional quantity of the disinfectant 20 when the disinfectant handle covering 10 is grasped. It relies, instead, on the transference to the hand of the user of a quantity of the disinfectant 20 that accumulates proximate the lower perforations 18, as identified by reference numeral 20a, to sterilize the user's hand.

If desired, a filler plug 30 (FIG. 1) is provided in an end member 32 that provides a seal at the open end 11a between the outer layer 14 and the inner layer 16. The filler plug 30 is removed (by unscrewing if secured by threads or pulling if secured by friction) when the quantity of the disinfectant in the inner reservoir 24 become sufficiently low and an additional quantity of the disinfectant 20 is added to fill the inner reservoir 24. The filler plug 30 is then replaced. If desired, the filler plug 30 is omitted and the disinfectant handle covering 10 is replaced when the disinfectant 20 in the inner reservoir 24 is exhausted.

Other methods of expelling a desired quantity of the disinfectant 20 at desired times are also possible. For example, an inflatable bladder 34 (FIG. 2) can be included in the inner reservoir 24 along with a motor 36 that drives a pump 38. The motor 36 is periodically activated which drives the pump 38. The pump 38 increasingly inflates the bladder 34 using air that is drawn in from an exterior location through an air inlet tube 39. As the bladder 34 inflates it applies increasing pressure to the disinfectant 20 in the inner reservoir 24, which urges (expels) a quantity of the disinfectant 20 out of the perforations 18.

The pump 38 operates off either batteries that may be contained in the disinfectant handle covering 10 or off of a low voltage direct current supply that converts 120 VAC into the desired low voltage direct current supply. The electrical wires that supply the low voltage direct current supply to the disinfectant handle covering 10 could be hidden along the handle 12 or contained in a modified form of the handle 12, if desired.

If desired, the motor 36 can be activated for a short amount of time at regular predetermined intervals of time that are selected to correspond appropriately to the human traffic and usage that is likely to occur (i.e., contact with the disinfectant handle covering 10) for any given period of time. If desired, a microprocessor is included and is preferably programmable. Therefore, the intervals between energizing of the motor 36 can be varied as often as possible during each day or for different days to accommodate expected variations in the amount of contact that is expected to occur with the handle 12 for any period of time. Similarly, the amount of time that the motor 36 is energized can also be varied (programmed) to control the amount of the disinfectant 20 that is expelled during each cycle of motor 36 activation.

In this way an automatic expelling of an ideal amount of the disinfectant 20 is provided that matches the average usage that is expected for the disinfectant handle covering 10.

If desired, a motion sensor 40 (FIG. 1) is provided proximate the handle 12. The motion sensor 40 detects when the hand of the user is approaching the disinfectant handle covering 10 and the motor 36 is energized for a predetermined period of time in response to a detection of the hand of the user by the motion sensor 40. This expels a predetermined quantity of the disinfectant 20 through the perforations 18 just prior to the user's hand making contact with the disinfectant handle covering 10, thereby ensuring the availability of the disinfectant 20.

In this way an automatic expelling of an ideal amount of the disinfectant 20 is provided that matches the actual real-time usage that is occurring for the disinfectant handle covering 10.

A further modification may be made to the disinfectant handle covering 10, as desired, in which the inflatable bladder 34, the motor 36, and the pump 38 can be eliminated from an interior of the disinfectant handle covering 10 and are replaced by a remote motor 36a and a remote pump 38a that are operatively connected to each other (as are the motor 36 and the pump 38). The remote motor 36a and the remote pump 38a are located at desired distance away from the disinfectant handle covering 10 (See FIG. 1 dashed lines).

An outer reservoir 42 (also shown in dashed lines) is provided at a location that is similarly disposed a desired distance away from the disinfectant handle covering 10. The outer reservoir 42 includes the disinfectant 20, in liquid or gel form, therein. Access to refill the reservoir 42 with the disinfectant 20, when necessary, is provided.

If desired, the remote motor 36a, the remote pump 38a, and the outer reservoir 42 can be attached to an inside of an enclosure 44, with the enclosure 44 mounted to an exterior of a wall or, alternately, the enclosure 44 can be located inside of a cabinet (not shown) or inside of a vanity (not shown) or other desired location or fixture. Access to an inside of the enclosure 44 is preferably restricted to permit only authorized personnel (owner, janitor, etc.) to service the remote motor 36a and the remote pump 38a and to periodically add a quantity of the disinfectant 20, when necessary, to the outer reservoir 42. (Temporarily refer to FIG. 3 reference numeral 60 which illustrates one possible way to restrict access.)

Preferably, the remote motor 36a and the remote pump 38a and the enclosure 44 (if used) are located as close to the disinfectant handle covering 10 as possible. If desired the remote motor 36a and the remote pump 38a (and the enclosure 44, if used) may be located in a recessed area or other space that is provided in the wall. Preferably, access to the recessed area or space would similarly be limited to authorized personnel (owner, janitor, etc.) only for servicing of the remote motor 36a and the remote pump 38a and for periodically adding a quantity of the disinfectant 20, when necessary, to the outer reservoir 42.

The remote pump 38a draws the disinfectant 20 from the outer reservoir 42 through an inlet conduit 46. When the remote motor 36a is energized, the disinfectant 20 is supplied under pressure by the remote pump 38a through an outlet conduit 48 to the inner reservoir 24.

When the motion sensor 40 detects the approach of the user's hand(s) toward the handle 12 or toward the disinfectant handle covering 10 an output signal, which occurs in response to each detection occurrence, is transmitted through an electrical wire 50 (or by wireless transmission, if preferred) to a control circuitry (not shown) that controls the remote motor 36a. The control circuitry may include any analog, digital, or microprocessor-based components, as preferred.

For each subsequent detection by the motion sensor 40 that occurs after a first predetermined period of time has elapsed without any detection of the hand(s) occurring, the control circuitry energizes the remote motor 36a for a predetermined period of time, for example, for a second or two, although the desired length of time that the remote motor 36a is energized can vary greatly. The time that the remote motor 36a is energized is a design variable which depends on several factors, including the quantity of the disinfectant 20 that is being supplied from the remote pump 38a per unit of time (i.e., the rate of flow of the disinfectant 20) and the size and configuration of the disinfectant handle covering 10.

Smaller types of the disinfectant handle covering 10 will require a smaller quantity of the disinfectant 20 to be supplied to the inner reservoir 24 for each usage than will larger versions of the disinfectant handle covering 10. When a version of the disinfectant handle covering 10 is used that includes the remote motor 36a, the remote pump 38a, and the outer reservoir 42 the motion sensor 40 is periodically activated a desired number of times to ensure that the inner reservoir 24 has been completely filled.

This is easily determined by observation of the exterior surface of the outer layer 14. After the inner reservoir 24 has been filled to capacity, each activation of the remote motor 36a will again supply an additional and predetermined quantity of the disinfectant 20 to the inner reservoir 24. As there is no remaining room in the inner reservoir 24, the additional quantity of the disinfectant 20 increases the pressure in the inner reservoir 24 and displaces an equivalent amount of the disinfectant 20 that is already in the inner reservoir 24 out of the inner reservoir 24 by forcing it out through the perforations (holes) 18 in the outer layer 14. When each activation cycle of the remote motor 36a produces a visible outflow of the disinfectant 20 to the exterior surface of the outer layer 14 it can be concluded that a sufficient number of activation cycles have occurred to prime the remote pump 38a, to prime and remove air from the inlet conduit 46 and the outlet conduit 48, and fill the inner reservoir 24.

The increasing pressure that the disinfectant 20 in the inner reservoir 24 is experiencing as a result of the inflow of the additional quantity of the disinfectant 20 is experienced simultaneously everywhere by the disinfectant 20 in the inner reservoir 24. Therefore, the disinfectant 20 bears with substantially equal pressure simultaneously on all of the perforations 18. Accordingly, the equivalent amount of the disinfectant 20 that is being displaced out of the inner reservoir 24 is expelled in a uniform and proportional manner through all of the perforations 18 simultaneously.

This provides an especially even distribution of the expelled disinfectant 20 over the exterior surface of the outer layer 14. This, in turn, ensures that an ample quantity of the disinfectant 20 will be transferred to the hand(s) of the user when contact is made with the disinfectant handle covering 10, thereby further increasing efficacy of the disinfectant handle covering 10 in preventing the spread of infection.

It is also important to note that the size of the perforations 18, as mentioned earlier, is a design variable. In particular, it is not required that all of the perforations 18 for any version of the disinfectant handle covering 10 (whether or not the version includes the motor 36, 36a or pump 38, 38a) be of identical size. For many versions, it is desirable to vary the quantity and size of the perforations that provided through the outer layer 14 to provide a way (method) of controlling the proportion of the disinfectant 20 that is being supplied to any given location on the exterior surface of the outer layer 14.

For certain versions of the disinfectant handle covering 10, a greater quantity of the disinfectant 20 is desired at locations that are more likely to be grasped by the user, for example, some of the more centralized locations on the top, front, and back and center portions of the exterior surface of the outer layer 14. It is less likely that any portion of the hand of the user will consistently make contact with the bottom of the outer layer 14 (that portion which is closest to the ground surface) or the extreme right and left ends thereof and, thereby, a lesser quantity of the disinfectant 20 is required at these locations.

Accordingly, smaller sizes or a lesser quantity of the perforations 18 can be provided where a slower rate of discharge of the disinfectant 20 is desired and larger sizes or a greater quantity of the perforations 18 can be provided where a greater (faster) rate of discharge of the disinfectant 20 is desired.

For certain other versions of the disinfectant handle covering 10, such as those designed for use with types of door handles that are pushed to open (as mentioned earlier) and which include a long and flat surface, the actual door handle may be pushed by the user at any location. For versions of the disinfectant handle covering 10 that are designed for use with these and other similar types of handles, the size and distribution of the perforations 18 is likely to be more uniform.

While also a design variable, it is not generally preferred that activation of the remote motor 36a will occur subsequent to every detection occurrence by the motion sensor 40. This is because a number of detection output signals may occur in response to the user moving his hands proximate the motion sensor 40 as he or she moves toward the disinfectant handle covering 10, grasps the outer layer 14, moves the handle 12 in the manner required to actuate whatever is controlled by the handle 12, releases the disinfectant handle covering 10, and withdraws.

Preferably, the remote motor 36a is energized by the control circuitry for each output signal that occurs after the first predetermined period of time has elapsed following the occurrence of the previous output signal. After the remote motor 36a has been energized, subsequent detections of the output signal that occur before the first predetermined period of time has elapsed do not result in additional activations of the remote motor 36a. This prevents the discharge of an excess quantity of the disinfectant 20 from occurring, which lowers operating cost and reduces the possibility of unsightly discharge and dripping of the disinfectant 20 off of the disinfectant handle covering 10. Ideally, the quantity of the disinfectant 20 that is supplied to the exterior surface of the outer layer 14 with each activation of the remote motor 36a is approximately equal to the quantity of the disinfectant 20 that is transferred to the hand or hands of the user as a result of the contact that occurs with the disinfectant handle covering 10 during activation of the handle 12 by the user.

Preferred operation for the motor 36 and the pump 38 is the same as was previously described for the remote motor 36a and the remote pump 38a except that the motor 36 and the pump 38 are integral component parts of the disinfectant handle covering 10 and are therefore located proximate the handle 12 instead of being located at a location that is away from the handle 12.

It is also possible that if the motor 36, 36a is energized for a predetermined amount of time at regular predetermined spaced-apart intervals that a sufficient quantity of the disinfectant 20 can be provided to the exterior surface of the outer layer 14 to provide a desired efficacy for any version of the disinfectant handle covering 10. Accordingly, for such versions the motion sensor 40 is eliminated and an interval timer is included in the control circuitry to periodically energize the motor 36, 36a at the desired spaced-apart intervals for the desired predetermined duration at each interval of time.

The various versions of the disinfectant handle covering 10 provide a method of reducing the spread of infectious diseases at low cost and which do not require that the user take any additional or unusual action than what is normally required to activate any given type of the handle 12. The fear of being infected is reduced in public places which provides many economic and humanitarian benefits.

For versions of the disinfectant handle covering 10 that include a flexible (soft) outer layer 14, the normal grasping and actuation motion of the handle 12 is sufficient to compress and expel a quantity of the disinfectant 20. For versions of the disinfectant handle covering 10 that include a rigid (hard) outer layer 14 and a method or means for expelling a quantity of the disinfectant 20 (such as the motor 36, 36a and the pump 38, 38a) the disinfectant 20 is expelled when approach of the user is detected or, alternately at regular spaced-apart intervals, thereby also eliminating the need for any additional (new type of) action by the user.

Referring again to FIG. 1, an alternate method for supplying a continuous amount of the disinfectant 20 to the disinfectant handle covering 10 is shown by providing a gravity-feed conduit 52 (shown in dashed lines). For this version of the disinfectant handle covering 10 (i.e., any version including the gravity-feed conduit 52) the remote motor 36a and the remote pump 38a are preferably omitted, although, if desired, they could also be included to provide an alternate or supplemental (i.e., additional) path for transferring a quantity of the disinfectant 20 from the outer reservoir 42 into the inner reservoir 24 to augment the rate of flow of the disinfectant 20 that is occurring through the gravity-feed conduit 52.

When the gravity-feed conduit 52 is used, the outer reservoir 42 is disposed at a higher elevation than the inner reservoir 24 and at a higher elevation that the outer layer 14. A minimum and maximum range in elevation that the outer reservoir 42 is disposed above the portion of the disinfectant handle covering 10 that is disposed proximate (i.e., around or attached to) the handle 12 is calculated for each version. The viscosity of the disinfectant 20 and the size and location of the perforations 18 are varied in order to provide the desired flow characteristics.

For most versions of the disinfectant handle covering 10, a preferred combination of all variables when the outer reservoir 42 is disposed above the inner reservoir 24 and when the force of gravity (alone) is being relied upon to convey the disinfectant 20 from the outer reservoir 42, through the gravity-feed conduit 52, and into the inner reservoir 24 will result in the accumulation of a desired quantity of the disinfectant 20 over at least some of the perforations 18 at an exterior of the outer layer 14 over the course of time.

When a sufficient accumulation has occurred, it is generally preferred that the surface tension of the disinfectant 20 and the exterior surface of the outer layer 14 is sufficiently strong to create stasis or equilibrium and stop any further flow of the disinfectant 20 through the perforations 18 and to also prevent a dripping of the disinfectant 20 that has accumulated over some of the perforations 18 off of the outer layer 14.

When a user makes contact with the handle 12, some of the accumulated disinfectant 20 is acquired by the hand(s) of the user and removed from the outer layer 14, thereby momentarily ending the condition of stasis or equilibrium until the force of gravity causes a further accumulation of the disinfectant 20 to occur primarily at those perforations 18 where it was removed by the user's hand(s), thereby restoring stasis or equilibrium. It is also possible that some additional accumulation will occur proximate some of the perforations 18 that the user did not contact, however, this amount is negligible.

The variables are controlled during design and installation to ensure that at least a desired minimum quantity but not more than a desired maximum quantity of the disinfectant 20 is able to flow through the perforations 18 within a predetermined given period of time. The range of rate of flow of the disinfectant 20 is, itself, a variable that is determined according to the anticipated rate of usage (i.e., contact) of the disinfectant handle covering 10, on average, that is likely to occur for any given installation, taking into account the traffic patterns, etc.

The use of the gravity-feed conduit 52 provides an especially green method of replenishing the disinfectant 20 available to the user by use of the force of gravity. For certain applications it may be preferred over other possible methods for the conveyance of the disinfectant 20.

If desired for gravity-feed applications, the perforations 18 at the bottom of the disinfectant handle covering 10 are enlarged to facilitate the accumulation of the disinfectant 20 proximate the bottom portion of the disinfectant handle covering 10. If it is further desired, all perforations 18 may be eliminated for gravity-feed applications other than those that are located proximate the bottom portion of the outer layer 14 of the disinfectant handle covering 10. If desired, any of the perforations 18 can be eliminated or enlarged to provide any desired distribution pattern for the disinfectant handle covering 10.

It is useful to note that when the remote motor 36a and the remote pump 38a are used to convey the disinfectant 20 without use of the gravity-feed conduit 52, the outer reservoir 42 can be disposed below the level of the inner reservoir 24, equal with the level of the inner reservoir 24, and to some extent it can be disposed above the inner reservoir 24. The amount it can be disposed above the inner reservoir 24 depends an several factors, including the viscosity of the disinfectant 20 that is used, the size and number of the perforations 18, and the overall resistance to the flow of the disinfectant 20 from the outer reservoir 42 to the exterior of the outer layer 14.

The maximum allowable elevation for the outer reservoir 42 with respect to the elevation of the disinfectant handle covering 10 must be set to prevent a continuous or excessive rate of flow of the disinfectant 20 from occurring through the disinfectant handle covering 10.

The maximum distance permissible for positioning the outer reservoir 42 below the inner reservoir 24 (i.e., below the disinfectant handle covering 10) depends on the remote pump's 38a output characteristics (i.e., pressure, rate of flow) in combination with the weight and viscosity of the disinfectant 20 and the overall resistance to flow (of the disinfectant 20) for any given version of the disinfectant handle covering 10 to ensure that at least a minimum desired quantity of the disinfectant 20 will be urged through the perforations 18 during each activation of the remote motor 36a and the remote pump 38a.

It is also possible to combine any version of the motor 36, 36a with any version of the pump 38, 38a to provide an integrated mechanism or means for urging a quantity of the disinfectant 20 from the outer reservoir 42 to the disinfectant handle covering 10 (if the remote motor 36a and the remote pump 38a are used) and ultimately to the exterior surface of the outer layer 14, or for urging the quantity of the disinfectant 20 from the inner reservoir 24 directly to the exterior surface of the outer layer 14 (if the motor 36 and the pump 38 are included in the portion of the disinfectant handle covering 10 that is disposed over, or proximate to the handle 12).

Similarly, the motor 36, 36a and the pump 38, 38a can be replaced by any device or method that is capable of urging (i.e., displacing) a desired quantity of the disinfectant 20 from the outer reservoir 42 to the inner reservoir 24 or from the inner reservoir 24 to the exterior surface of the outer layer 14.

Figure 3:
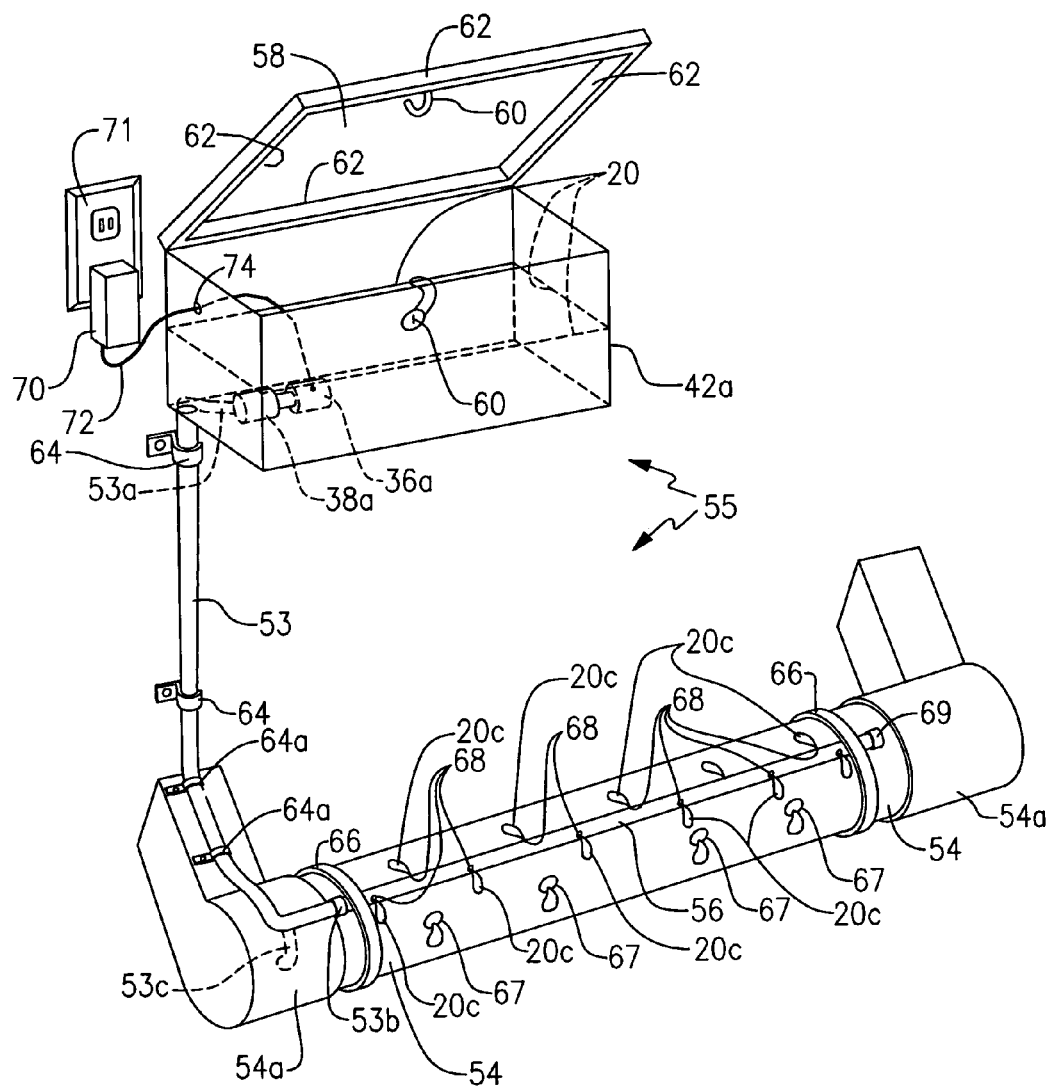
FIG. 3 is a view in perspective of a reservoir proximate a handle where the reservoir includes a quantity of disinfectant that is conveyed from the reservoir to a surface of the handle by various means.

Referring now to FIG. 3, a modified remote reservoir 42a is shown attached to a surface. The modified remote reservoir 42a is secured to the surface by fasteners, adhesive, or any other preferred method. If desired, the modified remote reservoir 42a is placed on a shelf that is attached to the surface.

The modified remote reservoir 42a is elevated a sufficient amount above any desired type of the handle 12. A type of an elongated handle 54 is shown to illustrate some of the variations possible for the handle 12 and how, by a modification of the disinfectant handle covering 10, a disinfecting handle system, identified in general by the reference numeral 55, is provided. The disinfecting handle system 55 applies a desired quantity of the disinfectant 20 directly to the exterior surface of any handle 12, including the elongated handle 54 to permit a desired rate of flow of the disinfectant 20 to occur from the modified remote reservoir 42a through a gravity-feed supply conduit 53 and into a drip assembly 56.

The modified remote reservoir 42a preferably includes a hinged lid 58 that is normally secured in a closed (or lowered) position and maintained by a locking mechanism 60 of a preferred type. When necessary, the hinged lid 58 is unlocked and is raised to add an additional quantity of the disinfectant 20 to the amount that is remaining in the modified remote reservoir 42a. The hinged lid 58 is then lowered and secured in a locked position by the locking mechanism 60 to prevent unwanted access.

The surface that the modified remote reservoir 42a is attached to may be fixed and unmoving, for example to a wall, or it may be attached to a moveable surface, such as to a door. To prevent spillage of the disinfectant 20 from the modified remote reservoir 42a a perimeter seal 62 can be included, as desired. The perimeter seal 62 is especially desirable if the modified remote reservoir 42a is attached to a moveable type of surface.

The gravity-feed supply conduit 53 is secured to the surface by clamps 64 or by any preferred adhesive or fastening method. If desired, modified clamps 64a or adhesive or other fastening method is used to secure the gravity-feed supply conduit 53 to a portion of the handle 54, 12.

An open first conduit end 53a of the gravity-feed supply conduit 53 is attached to a bottom of the modified remote reservoir 42a. For gravity-feed (only) versions the disinfectant 20 in the modified remote reservoir 42a flows into the first conduit end 53a, which is open and exposed to the disinfectant 20, under force supplied by gravity. As described hereinafter, other possible means are discussed for urging or conveying the disinfectant 20 from the modified remote reservoir 42a to the handle 54, 12 other than by reliance solely upon the force of gravity.

An open second conduit end 53b is distally disposed with respect to the first conduit end 53a. The second conduit end 53b supplies the disinfectant 20 to the drip assembly 56.

The drip assembly 56 is secured where desired to an active portion of the handle 54, 12 by circular clamps 66, such as are commonly used to bundle electrical wires together, by an adhesive, or any other fastening method.

The drip assembly 56 includes a plurality of openings 68 that are strategically located on the drip assembly 56 to direct in a controlled manner the discharge of a predetermined amount of the disinfectant 20c over the course of time to the exterior surface of the active portion of the handle 54, 12. The active portion refers to that portion of the handle 54, 12 that is normally or typically grasped by the user. If desired, the active portion can include any exposed portion of the handle 54, 12 including end mounting brackets 54a. In a manner similar to that as previously described, the size, quantity, and placement of the openings 68 is a variable that depends of various other factors, such as the viscosity of the disinfectant 20 and the desired flow rate, as well as the size of the handle 54, 12. An end cap 69 seals a distal end of the drip assembly 56.

If desired, it is also possible to modify the gravity-feed supply conduit 53 of the disinfecting handle system 55 to include a modified second conduit end 53c instead of the second conduit end 53b that supplies the disinfectant 20 to the drip assembly 56. The drip assembly 56 is also omitted. The modified second conduit end 53c supplies the disinfectant 20 directly into an interior of the handle 54, 12. This is possible for those types of the handle 54, 12 that are able to contain the disinfectant 20 therein and which can be modified to include a plurality of handle openings 67, where desired, through the handle 54, 12. Any desired quantity of the handle openings 67 may be provided at any desired location. Each of the handle openings 67 can include any desired size to optimally control the flow of the disinfectant 20 to the desired exterior locations of the handle 54, 12.

It is also possible to include the remote motor 36a and the remote pump 38a that is cooperatively attached to the remote motor 36a with any version of the disinfecting handle system 55 either in or proximate the modified remote reservoir 42a and to energize the remote motor 36a and the remote pump 38a for a predetermined period of time at predetermined spaced-apart intervals to deliver a desired quantity of the disinfectant 20 to the surface of the elongated handle 54 (or other handle 12), in a manner that is generally consistent with the teachings presented herein, and above.

Options for supplying electrical power to the remote motor 36a are the same as previously described for either the previously described applications utilizing the remote motor 36a as well as for those applications previously described utilizing the motor 36, and they include the use of replaceable or rechargeable batteries (located where preferred) or the use of a transformer 70 that converts the 120 VAC from a household outlet 71 to the low voltage, low current DC required by the remote motor 36*a*, and supplies the DC voltage and current to the remote motor 36*a* through a power supply wire 72 that passes through an opening and seal 74 that is provided through the modified remote reservoir 42*a*.

Similarly, it is possible to also include the sensor 40 for use in activating the remote motor 36*a* and the remote pump 38*a* for the predetermined period of time when approach of the user is detected by the sensor 40 to deliver the desired quantity of the disinfectant 20 to the surface of the elongated handle 54 (or other handle 12) prior to or at the time of contact by the user, again in a manner that is generally consistent with the teachings presented earlier herein. When the remote motor 36*a* and the remote pump 38*a* are used, an increased flexibility in the positioning of the modified remote reservoir 42*a* with respect to the elevation of the handle 54, 12 is also attained.

When included, the remote pump 38*a* supplies the disinfectant 20 into the first conduit end 53*a* at pressure. As noted above, when the remote pump 38*a* is not included the first conduit end 53*a* is open to the disinfectant 20.

If either the remote reservoir 42 or the modified remote reservoir 42*a* is not refillable with additional disinfectant 20, it is (or they are) replaced with a replacement reservoir (42, 42*a*) that is provided for this purpose. For some applications, use of the replacement reservoir (42, 42*a*) may be preferred as no transfer of the disinfectant 20 is required.

Other modifications are also possible the disinfecting handle system 55. For example, the routing and fastening of the supply conduit 53 can be varied to accommodate different any preferred style, size or type of the handle 12, 54 or to better hide it from view or possible contact. Similarly, the drip assembly 56 can be modified to include any preferred size or shape. For certain variations of the handle 12, 54 the drip assembly 56 can be modified to include any preferred form (i.e., it could be designed as a thin strip that encircles some of the active portion of the handle 12, 54, or it could be designed to include two or more parts [halves] that fasten together around a portion of the handle 12, 54, etc.) For certain other variations of the handle 12, 54 it may be desirable to include a plurality of the drip assemblies 56 in order to provide a more complete distribution of the disinfectant 20 over an active portion of the exterior surface of the handle 12, 54.

All versions of the disinfecting handle covering 10 provide the disinfectant 20 to an exterior surface of the outer layer 14 while all versions of the disinfecting handle system 55 provide the disinfectant 20 directly to an exterior surface of the handle 54, 12. Either approach ensures that the hands) of the user will contact at least some of the disinfectant 20 which is useful in reducing the spread of infection. Alternately, should the hand(s) of the user not actually make contact with a sufficient-enough quantity of the disinfectant 20 for any of the disinfectant 20 to be transferred to the hand(s) of the user, it is likely that any germs or other pathogens that were deposited on either the disinfectant handle covering 10 or on the exterior surface of the handle 54, 12 by an infected person will have been killed or sufficiently weakened by the residual disinfectant 20 or vapors thereof to significantly reduce the possibility of the spread of infection.

The invention has been shown, described, and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. A disinfectant handle covering for use with a handle, comprising:

a) a covering that is disposed over at least a portion of the handle;
    b) means for securing said covering to the handle;
    c) means for containing a quantity of a disinfectant in an interior portion of said covering; and
    d) means for urging a predetermined amount of said disinfectant from said interior portion to an exterior portion of said covering;
    wherein said means for urging a predetermined amount of said disinfectant includes a pump, wherein an activation of said pump urges said predetermined amount of said disinfectant to said exterior portion, and wherein said pump is activated for a predetermined duration of time in response to an activation of a sensor, and wherein said sensor is disposed proximate the handle, and wherein said activation of said sensor occurs in response to sensing the approach of a person toward the handle.

2. The disinfectant handle covering of claim 1 wherein said means for containing said quantity of said disinfectant in said interior portion of said covering includes an inner reservoir.

3. The disinfectant handle covering of claim 2 wherein said inner reservoir is disposed between an outer layer of said disinfectant handle covering and an inner layer of said disinfectant handle covering, wherein said inner layer is disposed proximate an exterior surface of the handle.

4. The disinfectant handle covering of claim 1 wherein said means for urging a predetermined amount of said disinfectant from said interior portion to said exterior portion of said covering includes an outer layer of said disinfectant handle covering that includes at least one opening there-through, and wherein said outer layer is sufficiently flexible to permit a portion thereof to flex in an inward direction in response to a compressive force being applied to said outer layer when a user grasps said outer layer or applies a force to said outer layer, and wherein when a portion of said outer layer is flexed in an inward direction, said predetermined amount of said disinfectant is urged from said interior portion to said exterior portion.

5. The disinfectant handle covering of claim 4 including means for replenishing at least a portion of said disinfectant in said interior portion when a sufficient amount of said disinfectant in said interior portion has been urged to said exterior portion of said disinfectant handle covering.

6. The disinfectant handle covering of claim 4 wherein when a sufficient amount of said disinfectant in said interior portion has been urged to said exterior portion of said disinfectant handle covering, said disinfectant handle covering is replaced.

7. The disinfectant handle covering of claim 1 wherein subsequent to said activation of said pump, a pressure of said disinfectant in said interior portion is increased an amount sufficient to urge a portion of said disinfectant from said interior portion to said exterior portion through at least one opening that is provided in said covering.

8. The disinfectant handle covering of claim 7 including a motor cooperatively connected with said pump, wherein an energizing of said motor produces said activation of said pump.

9. The disinfectant handle covering of claim 8 wherein said motor is energized for a predetermined duration of time at predetermined spaced-apart intervals of time.

10. The disinfectant handle covering of claim 8 wherein said motor is energized for a predetermined duration of time in response to said activation of said sensor.

11. The disinfectant handle covering of claim 10 wherein said sensor includes a motion sensor.

12. The disinfectant handle covering of claim 1 including an outer reservoir, and wherein said outer reservoir includes a quantity of said disinfectant, and wherein said outer reservoir is disposed a predetermined distance away from the handle, and wherein said outer reservoir includes a conduit for supplying said quantity of said disinfectant to said interior portion.

13. The disinfectant handle covering of claim 1 wherein said disinfectant includes a liquid or a gel.

14. A method for applying a quantity of a disinfectant to a surface of a handle or to a surface of a covering of the handle, comprising the steps of:
   a) providing a container for housing the quantity of the disinfectant; and
   b) providing means for urging a portion of the quantity of the disinfectant from an interior of the handle or covering to an exterior of the handle or covering;
   wherein said means for urging includes a pump, wherein an activation of said pump urges said predetermined amount of said disinfectant from said container to the surface, and wherein said pump is activated for a predetermined duration of time in response to an activation of a sensor, and wherein said sensor is disposed proximate the handle, and wherein said activation of said sensor occurs in response to sensing the approach of a person toward the handle, wherein said disinfectant is urged to the surface prior to said person making contact with the handle.

15. The method of claim 14 wherein the step of providing means for urging a portion of the quantity of the disinfectant from the container to the surface includes the step of providing means for urging a portion of the quantity of the disinfectant from the container to an exterior surface of an outer layer of a disinfectant handle covering or to an exterior surface of a handle.

\* \* \* \* \*